(12) United States Patent
Gregersen et al.

(10) Patent No.: US 11,219,406 B2
(45) Date of Patent: Jan. 11, 2022

(54) DEVICES FOR TESTING DISTAL COLONIC AND ANORECTAL FUNCTION

(71) Applicant: GI Bionics LLC, San Diego, CA (US)

(72) Inventors: Hans Gregersen, Ma On Shan (HK); Ghassan S. Kassab, La Jolla, CA (US)

(73) Assignee: GI Bionics LLC, San Diego, CA (US)

( * ) Notice: Subject to any disclaimer, the term of this patent is extended or adjusted under 35 U.S.C. 154(b) by 1035 days.

(21) Appl. No.: 15/664,938

(22) Filed: Jul. 31, 2017

(65) Prior Publication Data

US 2017/0340264 A1  Nov. 30, 2017

Related U.S. Application Data

(63) Continuation-in-part of application No. 15/521,297, filed as application No. PCT/US2015/056777 on Oct. 21, 2015.

(Continued)

(30) Foreign Application Priority Data

Oct. 22, 2014   (CN) .......................... 201420612247.4

(51) Int. Cl.
*A61B 5/00*       (2006.01)
*A61B 5/0538*     (2021.01)
(Continued)

(52) U.S. Cl.
CPC .......... *A61B 5/4255* (2013.01); *A61B 5/0538* (2013.01); *A61B 5/1076* (2013.01);
(Continued)

(58) Field of Classification Search
CPC ... A61B 5/4255; A61B 5/6861; A61B 5/6873; A61B 5/036; A61B 5/1107
See application file for complete search history.

(56) References Cited

U.S. PATENT DOCUMENTS 6,584,348 B2   6/2003  Glukhovsky
7,970,455 B2 *  6/2011  Zilberstein ......... A61B 1/00156
                                                          600/411

(Continued)

FOREIGN PATENT DOCUMENTS

CN         204181752 U        3/2015

OTHER PUBLICATIONS

Bharucha, AE et al. "Anorectal disorders." Am. J Gastroenterol., Apr. 2010, vol. 105, No. 4, pp. 1-15.

(Continued)

*Primary Examiner* — Carrie R Dorna
(74) *Attorney, Agent, or Firm* — Reichel Stohry Dean LLP; Mark C. Reichel; Natalie J. Dean

(57) ABSTRACT

Devices for testing distal colonic and anorectal function. In at least one embodiment of a device of the present disclosure, the device comprises a flexible central support, a first bag or balloon surrounding at least part of the flexible central support; and a first plurality of sensors positioned upon or embedded within a surface of the first bag or balloon, each of the first plurality of sensors positioned a known distance from each other; wherein the first plurality of sensors are configured to obtain pressure measurements on the surface of the first bag or balloon when the device is operated within a mammalian gastrointestinal tract.

18 Claims, 15 Drawing Sheets

Related U.S. Application Data

(60) Provisional application No. 62/369,185, filed on Jul. 31, 2016, provisional application No. 62/243,051, filed on Oct. 17, 2015, provisional application No. 62/239,034, filed on Oct. 8, 2015.

(51) Int. Cl.
*A61B 5/107* (2006.01)
*A61B 5/22* (2006.01)

(52) U.S. Cl.
CPC ............ *A61B 5/227* (2013.01); *A61B 5/6873* (2013.01); *A61B 2562/0247* (2013.01)

(56) References Cited

U.S. PATENT DOCUMENTS

2004/0230131 A1* 11/2004 Kassab ................. A61B 5/053
600/547
2007/0161885 A1* 7/2007 Kimchy ................. A61B 5/42
600/407
2009/0118637 A1 5/2009 Kassab et al.
2016/0029998 A1* 2/2016 Brister ................. A61B 1/041
600/424

OTHER PUBLICATIONS

Dall, FH et al. "Biochemical wall properties of the human rectum—a study with impedance planimetry." Gut, Nov. 1993, vol. 34, No. 11, pp. 1581-1586.
Patent Cooperation Treaty (PCT), International Searching Authority, International Search Report, PCT/US2015/056777, dated Mar. 29, 2016.
Patent Cooperation Treaty (PCT), International Searching Authority, Written Opinion of the International Searching Authority, PCT/US2015/056777, dated Mar. 29, 2016.

* cited by examiner $P_0$=PRE-EXPULSION PHASE
$P_1$=ABDOMINAL PRESSURE INCREASE
$P_2$=ANAL SPHINCTER RELAXATION
$P_3$=FRONT OUT OF ANAL CANAL
$P_4$=REAR END PASSAGE
$P_5$=POST-EXPULSION

DEVICES FOR TESTING DISTAL COLONIC AND ANORECTAL FUNCTION

RELATED APPLICATIONS

The present application 1) is related to, and claims the priority benefit of, U.S. Provisional Patent Application Ser. No. 62/369,185, filed Jul. 31, 2016, and 2) is related to, claims the priority benefit of, and is a U.S. continuation-in-part patent application of, U.S. patent application Ser. No. 15/521,297, filed Apr. 23, 2017, which is related to, claims the priority benefit of, and is a U.S. §371 national stage patent application of, International Patent Application Serial No. PCT/US2015/056777, filed on Oct. 22, 2015, which is related to, and claims the priority benefit of, a) China Patent Application Serial No. 2014 2 0612247.4, filed on Oct. 22, 2014, b) U.S. Patent Application Ser. No. 62/239,034, filed on Oct. 8, 2015, and c) U.S. Patent Application Ser. No. 62/243,051, filed on Oct. 17, 2015. The contents of each of the aforementioned patent applications are incorporated herein in their entirety.

BACKGROUND

The function of visceral organs like the gastrointestinal tract, the urinary tract and the heart or blood vessels is to a large degree mechanical. The following introduction refers mainly to the gastrointestinal tract but the invention relates to similar applications in other hollow organs such as the urinary tract and the biliary system in humans and animals.

The gastrointestinal tract is a long tube where ingested food is digested. Feces is formed from digested contents, from secretions and from micro-organisms in the distal part of the gastrointestinal tract. Muscle activity in the wall of the large intestine (so-called high amplitude propagated (contractile) sequences) pushes the fecal contents more distal and at some point when it reach the sigmoid colon, the person or animal feels urge to defecate, go to the restroom and expel the fecal contents as a voluntary action where the abdominal pressure is increased, the ano-rectal angle changes, and the anal sphincters relax. The biomechanical properties including the muscle contractile function and neural circuits (reflexes) are very important for this process.

The Specific Problem and Current Solutions.

The defecatory function is very complex which has two implications, 1) it is difficult to study the process in detail and 2) in many persons defecation is not functioning the way it should, for example many patients in China and Worldwide, especially elderly persons, suffer from constipation where they have difficulties to defecate. Whereas it is normal for most persons to defecate every day or every second day, constipated patients may only be able to do it once weekly or even more seldom.

Constipation can have many courses. For example it relates to hyposensitivity of nerve fibers or to lack of dietary fibers in the food. Since constipation and also other defecatory problems, such as pain during defecation, fecal incontinence, Hirschsprungs disease, extreme urge to defecate or diarrhea, are frequent diseases in the population, it is of great importance to measure and analyse data related to the defecatory process. Disordered defecation and incontinence are associated with significant economic and personal burdens. Our understanding of defecation is incomplete which at least in part rely on lack of appropriate investigatory tools.

Treatment of defecation problems rely on proper diagnosis. Treatments can be surgery, medical treatment or biofeedback. Defecation can be studied in specialized units in hospitals by means of several methods such as pressure recordings (manometry), balloon distension, endoscopy, ultrasonography, and radiographic examinations (defecography). Although these methods provide data on the function, they do not provide good measures of the forces the feces is exposed to and the resultant displacements. Most of the methods record only a few parameters and from one part of the system (for example only from the rectum or from the anal canal). Also symptoms usually do not correlate well to results from these tests and therefore the clinical value is limited. Other devices such as an ingestible capsula has been commercialised to measure the transit and pressures during passage from the esophagus to the anus. The commercialized capsula may record pressures and pH and may take photos throughout the passage of the gastrointestinal tract but it has limited use for evaluating defecatory function.

It will be an advantage with more advanced technology for diagnosing disordered defecation. Needless to say for clarifying mechanisms of dysfunction in patients such a device must make recordings during the passage from the sigmoid colon to the rectum and the anal canal. It should be as natural as possible, in other words imitate the normal feces and the defecation process, and provide measurements of forces, deformation, location and flow for detailed analysis of the process. The preferred embodiment of the present invention is an intraluminal solid or semisolid feces-like device with multiple sensors for analysis of the defecation process.

BRIEF SUMMARY

The invention consists of an electro-mechanical device that preferentially can be inserted into the rectum or colon for studying the mechanics of defecation. The device, in various embodiments, is semi-solid, bendable and compressible in order to have the same consistency as feces, and it contains a variety of sensors such as pressure sensors, force sensors, deformation sensors, gyroscopes, accelerometers and possible also imaging devices. It also contains energy supply for the electronic sensors. It may either contain means for storage of data or for wireless transmission of data to an external recording device. After insertion into the intestine, preferably in the sigmoid colon, the device can be expanded and decoupled from the insertion device. When the person being studied feels an urge to defecate, he or she will expel it. During this process the device can measure a variety of parameters such as pressure profiles, compression strain, bending, orientation, location, acceleration and flow, providing very detailed data on the defecation process. Detailed analysis of the data can be done by means of software programs. The distribution of signals, the shape of the device and position may be used to generate a graphical image of the passage of the device in the distal colon, rectum and anal canal.

In at least one embodiment of a device configured for insertion into a gastrointestinal tract of the present disclosure, the device comprises a core comprising a core material which is solid, semi-solid or compressible, one or more sensors embedded in an interior of the device and/or on a surface of the device, at least one of the one or more sensors configured to obtain a pressure measurement within the gastrointestinal tract and during defecation of the device, and a plurality of electrodes within or upon the device and configured to obtain impedance planimetric measurements within the gastrointestinal tract and during defecation of the device, the impedance planimetric measurements useful to determine cross-sectional areas.

In at least one embodiment of a device configured for insertion into a gastrointestinal tract of the present disclosure, the device further comprises a central support that stabilizes and supports the device while providing bending flexibility for the device to have comparable mechanical properties to normal feces.

In at least one embodiment of a device configured for insertion into a gastrointestinal tract of the present disclosure, the device further comprises an outer sizable structure comprising a bag or balloon around the core and configured to retain liquid or gas therein.

In at least one embodiment of a device configured for insertion into a gastrointestinal tract of the present disclosure, the central support is stiff or bendable. In at least one embodiment of a device configured for insertion into a gastrointestinal tract of the present disclosure, the core is compressible.

In at least one embodiment of a device configured for insertion into a gastrointestinal tract of the present disclosure, the central support, the core, or the outer sizable structure are at or between 3-10 cm long.

In at least one embodiment of a device configured for insertion into a gastrointestinal tract of the present disclosure, the device further comprises one or more additional sensors selected from the group consisting of force sensors, strain gauges, location sensors, gyroscopes, bending sensors, deformation sensors, accelerometers, and cameras.

In at least one embodiment of a device configured for insertion into a gastrointestinal tract of the present disclosure, the central support, the core, or the outer sizable structure are at or between 3-10 cm long.

In at least one embodiment of a device configured for insertion into a gastrointestinal tract of the present disclosure, the device further comprises one or more additional sensors selected from the group consisting of pressure transducers, force sensors, strain gauges, location sensor, gyroscopes, bending sensors, deformation sensors, accelerometer, and miniature cameras for measurement of organ function.

In at least one embodiment of a device configured for insertion into a gastrointestinal tract of the present disclosure, the device further comprises an energy source.

In at least one embodiment of a device configured for insertion into a gastrointestinal tract of the present disclosure, the device further comprises a data storage unit.

In at least one embodiment of a device configured for insertion into a gastrointestinal tract of the present disclosure, the device further comprises a wireless transmission unit configured to communicate with an external receiver.

In at least one embodiment of a device configured for insertion into a gastrointestinal tract of the present disclosure, the device forms a system along with a display, a signal conditioning unit, and an analysis unit, wherein data obtained from the one or more sensors and/or the plurality of electrodes can be analyzed in terms of trajectories, force distributions, bending, angling, color contour plots, and/or 3D (three-dimensional) graphics, for transit function in an organ.

In at least one embodiment of a device configured for insertion into a gastrointestinal tract of the present disclosure, the device is configured for placement within the sigmoid colon or rectum and where the core material and the surface of the device have comparable properties to feces.

In at least one embodiment of a device configured for insertion into a gastrointestinal tract of the present disclosure, the device comprises a valve configured to connect to a tube, the tube used to provide the outer sizable structure with the liquid or the gas.

In at least one embodiment of a device configured for insertion into a gastrointestinal tract of the present disclosure, the device further comprises an attachment configured to permit an individual inserting the device into the gastrointestinal tract to push or pull the device to a preferred location.

In at least one embodiment of a device configured for insertion into a gastrointestinal tract of the present disclosure, the device is configured to be inserted into the gastrointestinal tract using an introducer that will be withdrawn from the device before operation of the device within the gastrointestinal tract.

In at least one embodiment of a device configured for insertion into a gastrointestinal tract of the present disclosure, the device comprises a long and narrow configuration.

In at least one embodiment of a device configured for insertion into a gastrointestinal tract of the present disclosure, the device further comprises one or more electrical stimulating sensors thereon, the one or more electrical stimulating sensors configured to deliver an electrical signal to a portion of the gastrointestinal tract.

In at least one embodiment of a device configured for insertion into a gastrointestinal tract of the present disclosure, the device further comprises a battery or energy source connected via wires to the one or more sensors and to the plurality of electrodes.

In at least one embodiment of a device configured for insertion into a gastrointestinal tract of the present disclosure, the device further comprises a stabilizing flexible or non-flexible core rod.

In at least one embodiment of a device configured for insertion into a gastrointestinal tract of the present disclosure, the device further comprises a stabilizing flexible or non-flexible core rod.

In at least one embodiment of a device configured for insertion into a gastrointestinal tract of the present disclosure, the battery or energy source is coupled to the stabilizing flexible or non-flexible core rod.

The present disclosure includes disclosure of use of any of the various device embodiments of the present disclosure.

In at least one use of an exemplary device of the present disclosure, the outer sizable structure can be inflated at different pressures and/or volumes and wherein diameters of the outer sizable structure can be recorded at the different pressures and/or volumes.

In at least one use of an exemplary device of the present disclosure, the diameters can be recorded as a circumference and a tension to produce a tension-length relation.

In at least one use of an exemplary device of the present disclosure, pressure measurements and impedance measurements can be obtained by the device within the gastrointestinal tract and during defecation of the device.

In at least one use of an exemplary device of the present disclosure, the pressure measurements and/or the impedance measurements obtained within the gastrointestinal tract and/or during defecation of the device can be used to diagnose a gastrointestinal condition.

In at least one embodiment of a device of the present disclosure, the device comprises a flexible central support; a first bag or balloon surrounding at least part of the flexible central support; and a first plurality of sensors positioned upon or embedded within a surface of the first bag or balloon, each of the first plurality of sensors positioned a known distance from each other; wherein the first plurality of sensors are configured to obtain pressure measurements on the surface of the first bag or balloon when the device is operated within a mammalian gastrointestinal tract.

In at least one embodiment of a device of the present disclosure, the first bag or balloon is configured for self-expansion.

In at least one embodiment of a device of the present disclosure, the device further comprises a quantity of a first chemical and a quantity of a second chemical within the first bag or balloon.

In at least one embodiment of a device of the present disclosure, a reaction between the quantity of the first chemical and the quantity of the second chemical causes a quantity of a gas to be generated, whereby the quantity of the gas causes the first bag or balloon to inflate.

In at least one embodiment of a device of the present disclosure, the device further comprises a second bag or balloon surround at least another part of the flexible central support; and a second plurality of sensors positioned upon or embedded within a surface of the second bag or balloon, each of the second plurality of sensors positioned a known distance from each other; wherein the second plurality of sensors are configured to obtain additional pressure measurements on the surface of the second bag or balloon when the device is operated within a mammalian gastrointestinal tract.

In at least one embodiment of a device of the present disclosure, the second bag or balloon is configured for self-expansion.

In at least one embodiment of a device of the present disclosure, the device further comprises an additional quantity of the first chemical and an additional quantity of the second chemical within the second bag or balloon.

In at least one embodiment of a device of the present disclosure, wherein a reaction between the additional quantity of the first chemical and the additional quantity of the second chemical causes an additional quantity of the gas to be generated, whereby the additional quantity of the gas causes the second bag or balloon to inflate.

In at least one embodiment of a device of the present disclosure, the device is sized and shaped to be swallowed by a mammal.

In at least one embodiment of a device of the present disclosure, the device further comprises a solid or semi-solid material positioned within the first bag or balloon that at least partially surrounds at least part of the flexible central support.

In at least one embodiment of a device of the present disclosure, the device further comprises a first plurality of electrodes configured to obtain impedance measurements indicative of cross-sectional areas at various locations within the first bag or balloon when the device is operated within the mammalian gastrointestinal tract.

In at least one embodiment of a device of the present disclosure, the device further comprises a second plurality of electrodes configured to obtain additional impedance measurements indicative of additional cross-sectional areas at various locations within the second bag or balloon when the device is operated within the mammalian gastrointestinal tract.

In at least one embodiment of a device of the present disclosure, the device is configured to transmit the pressure measurements and the impedance measurements indicative of the cross-sectional areas to an external device configured to receive the pressure measurements and the impedance measurements indicative of the cross-sectional areas and further configured to generate a two-dimensional or a three-dimensional image depicting the pressure measurements and the cross-sectional areas at various locations within the device when the device is operated within the mammalian gastrointestinal tract.

In at least one embodiment of a device of the present disclosure, a first pressure measurement within the pressure measurements is indicative of pressure exerted upon the device by the mammalian gastrointestinal tract prior to excretion, and wherein a second pressure measurement within the pressure measurements is indicative of pressure exerted upon the device by the mammalian gastrointestinal tract during excretion, and wherein the first pressure measurement is higher than the second pressure measurement.

In at least one embodiment of a method of obtaining pressure measurements of the present disclosure, the method comprising the step of positioning an exemplary device of the present disclosure within the mammalian gastrointestinal tract; and operating the device to obtain the pressure measurements within the mammalian gastrointestinal tract.

In at least one embodiment of a device of the present disclosure, the device comprises a flexible central support; a first bag or balloon surrounding at least part of the flexible central support; a first plurality of sensors positioned upon or embedded within a surface of the first bag or balloon, each of the first plurality of sensors positioned a known distance from each other; and a quantity of a first chemical and a quantity of a second chemical within the first bag or balloon; wherein the first plurality of sensors are configured to obtain pressure measurements on the surface of the first bag or balloon when the device is operated within a mammalian gastrointestinal tract; wherein a reaction between the quantity of the first chemical and the quantity of the second chemical causes a quantity of a gas to be generated, whereby the quantity of the gas causes the first bag or balloon to inflate; and wherein the device is sized and shaped to be swallowed by a mammal.

In at least one embodiment of a device of the present disclosure, the device further comprises a solid or semi-solid material positioned within the first bag or balloon that at least partially surrounds at least part of the flexible central support.

In at least one embodiment of a device of the present disclosure, the device further comprises a first plurality of electrodes configured to obtain impedance measurements indicative of cross-sectional areas at various locations within the first bag or balloon when the device is operated within the mammalian gastrointestinal tract.

In at least one use of an exemplary device of the present disclosure, a length (from circumference or diameter) and tension (from the product of pressure and diameter) can be determined using measurements obtained by the device. Various devices of the present disclosure, and uses thereof, as referenced herein, may not have a bag or balloon but are configured to obtain impedance, pressure, and/or other measurements as referenced herein. As an example of a device without a bag mounted, the core may contain closely spaced pressure sensors on the surface to collect detailed high-resolution pressure profiles when located inside the body or during the expulsion of the device for display of color contour graphs. Various devices of the present disclosure, and uses thereof, as referenced herein, can be configured to obtain pressure measurements on the surface of the bag or balloon as referenced herein. Various devices of the present disclosure, as referenced herein, are configured wherein the balloon or bag is configured for self-expansion, such as by way of a reaction between a first chemical and a second chemical within the balloon or bag that releases a gas that inflates the balloon or bag, as referenced herein. Various devices of the present disclosure, as referenced herein, can have two or more balloons or bags, with various components within or upon the surface of the balloons or bags. Various devices of the present disclosure, as referenced herein, can be sized and shaped to be swallowed. The various embodiments of the present disclosure will provide a wealth of data related to the function of the organ, in particular to the fecal expulsion process. Pressures, dimensional changes and other measures may be displayed as still pictures or as a function of time, such as in video representations or color contour plots. The data may be analysed further and displayed in multiple ways, as an example the pressures measured at the front end and the rear end of the core may be displayed as X-Y plots (front pressure vs rear pressure) which will create loop curves where the magnitude of the pressures and the shape of the loop will show normal patterns of defecation as well as specific patterns for defecation in patients with obstructed defecation or with fecal incontinence. Another example of analysing the front and rear pressures are to display these pressures as function of time and include calculations of differential pressures. This facilitates dividing the defecation process into multiple phases that indicates various physiological phenomena such as abdominal and rectal muscle contractions, anal sphincter relaxation or paradoxical contraction, velocity of expulsion in the different phases. The abovementioned data can be analysed merely from two pressures since the distance between the pressure sensors are known. It is clear that the arsenal of analysis will increase tremendously when combined with more pressure measurements, dimensional data, gyroscope data and other measures. A very detailed characteristic of gastrointestinal function, in particular defecation, can be provided.

BRIEF DESCRIPTION OF THE DRAWINGS

The disclosed embodiments and other features, advantages, and disclosures contained herein, and the matter of attaining them, will become apparent and the present disclosure will be better understood by reference to the following description of various exemplary embodiments of the present disclosure taken in conjunction with the accompanying drawings, wherein:

In FIG. 1A the device is shown in the sigmoid colon immediately after insertion. In FIG. 1B the device is passing down into the rectum and the anorectal angle is changed as it does during defecation. In FIG. 1C the device is about to be expelled through the anal canal. The elements as shown in these figures include 1: smart artificial pellet device (SAP), 2: anal sphincter, 3: rectum, 4: sigmoid colon, and 5: anorectal angle.

In FIG. 2A the artificial fecal pellet has a stabilizing flexible core in the interior which allows it to bend in different directions. In FIG. 2B an embodiment is shown without the central structure. FIG. 2C shows an embodiment with an outer balloon that can be inflated until the patient feel urge to defecate or experience other symptoms. FIG. 2D shows the connecting tube and an exemplary valve that is used during filling of the balloon. When the tube is disconnected, the valve secures that the fluid inside the balloon does not leak out. FIG. 2D also illustrates a loop structure at the tip which can be used for the doctor to drag the artificial fecal pellet with an endoscope up to the preferred location. FIG. 2E illustrates a device (artificial fecal pellet) having two portions, namely a portion with a first bag or balloon and elements therein as shown in FIG. 2C, for example, and a second portion with a second bag or balloon and elements therein also as shown in FIG. 2C, for example. Such an embodiment comprises two bags or balloons and could comprise three or more bags or balloons in other embodiments. Such embodiments could have one or more pressure sensors therein or on the surface of the bag, and would have impedance electrodes in or on each bag as well. The elements as shown in these figures include 6: central stabilizing flexible or non-flexible core rod, 7: pellet solid or semi-solid material, 8: sensors embedded in the interior of the artificial fecal pellet, 9: sensor on the surface of the artificial fecal pellet, 10: battery or energy source connected through wires to all sensors, transducers and transmitter, 11: data storage device or wireless transmitter to outside unit, 12: distensible shell like a balloon or bag that can be inflated, 13: liquid or gas inside the shell, 14: electrodes for impedance planimetric measurement of cross-sectional areas, 15: loop that the endoscope can attach to during insertion, 16: valve, and 17: tube for filling the outer structure such as a balloon.

In FIG. 5A the pellet further comprises one or more electrical stimulating sensors on the surface of the artificial fecal pellet. FIG. 5B shows an embodiment without a distensible shell like a balloon or bag that can be inflated, whereby the sensors embedded in the interior of the artificial fecal pellet, the battery, and the data storage device or wireless transmitter to outside unit are positioned on or within the central stabilizing flexible or non-flexible core rod. The elements as shown in these figures include 6: central stabilizing flexible or non-flexible core rod, 7: pellet solid or semi-solid material, 8: sensors embedded in the interior of the artificial fecal pellet, 9: sensor on the surface of the artificial fecal pellet, 10: battery or energy source connected through wires to all sensors, transducers and transmitter, 11: data storage device or wireless transmitter to outside unit, and 22: electrical stimulating sensor on the surface of the artificial fecal pellet.

In FIG. 6A the pellet further comprises at least one sensor configured as a camera and a light source, such as a flash, so to provide light so that the camera can obtain images within the patient. FIG. 6B shows an embodiment whereby the smart artificial pellet can make movements and thereby crawl in a direction within the body, such as up the colon, using a movement device and a motor. The elements as shown in these figures include 6: central stabilizing flexible or non-flexible core rod, 7: pellet solid or semi-solid material, 8: sensors embedded in the interior of the artificial fecal pellet, 9: sensor on the surface of the artificial fecal pellet, 10: battery or energy source connected through wires to all sensors, transducers and transmitter, 11: data storage device or wireless transmitter to outside unit, 23: sensor configured as a camera, 24: light source, such as a flash, 25: movement device, and 26: motor.

In FIG. 7A the pellet further comprises a bag or balloon positioned around the front and rear (proximal and distal) sensors configured as pressure transducers in order to measure a more reliable pressure during expulsion, such as shown in FIG. 1C. FIG. 7B shows an embodiment whereby certain components (the battery or energy source and the data storage device or wireless transmitter shown as exemplary components) are external to the pellet but connected to the pellet using thin wires. The elements as shown in these figures include 6: central stabilizing flexible or non-flexible core rod, 7: pellet solid or semi-solid material, 8: sensors embedded in the interior of the artificial fecal pellet, 9: sensor on the surface of the artificial fecal pellet, 10: battery or energy source connected through wires to all sensors, transducers and transmitter, 11: data storage device or wireless transmitter to outside unit, 27: bag or balloon positioned around a sensor; 28: liquid or gas inside the bag or balloon; and 29: wire.

In FIG. 8A the pellet further comprises an application-specific integrated circuit (ASIC) or printed circuit whereby one or more of the embedded sensor, the battery or energy source, the data storage device or wireless transmitter, and/or the electrodes for impedance measurements, are positioned thereon and/or otherwise coupled thereto. Such embodiments can comprise a processor configured to process the various types of data obtained using the various sensors and/or electrodes, and that data (processed and/or raw) can be stored within a storage medium, such as memory, of the device. FIG. 8B shows an embodiment whereby one or more magnets or magnetically-attractive elements can be used so to magnetically attach to an endoscope during insertion and/or to the tube for filling the outer structure such as a balloon. Alternatively, and instead of using a tube for filling the balloon, a first chemical and a second chemical could be positioned within the bag or balloon, and a reaction between the first chemical and the second chemical could release a gas that is used to expand the balloon, as referenced in further detail herein. The elements as shown in these figures include 6: central stabilizing flexible or non-flexible core rod, 7: pellet solid or semi-solid material, 8: sensors embedded in the interior of the artificial fecal pellet, 9: sensor on the surface of the artificial fecal pellet, 10: battery or energy source connected through wires to all sensors, transducers and transmitter, 11: data storage device or wireless transmitter to outside unit, 12: distensible shell like a balloon or bag that can be inflated, 13: liquid or gas inside the shell, 14: electrodes for impedance planimetric measurement of cross-sectional areas, 16: valve, 17: tube for filling the outer structure such as a balloon, 30: application-specific integrated circuit or printed circuit, 31: processor, 32: storage medium; 33: magnet or magnetically-attractive element; 40: first chemical; and 41: second chemical.

Figure 1A:
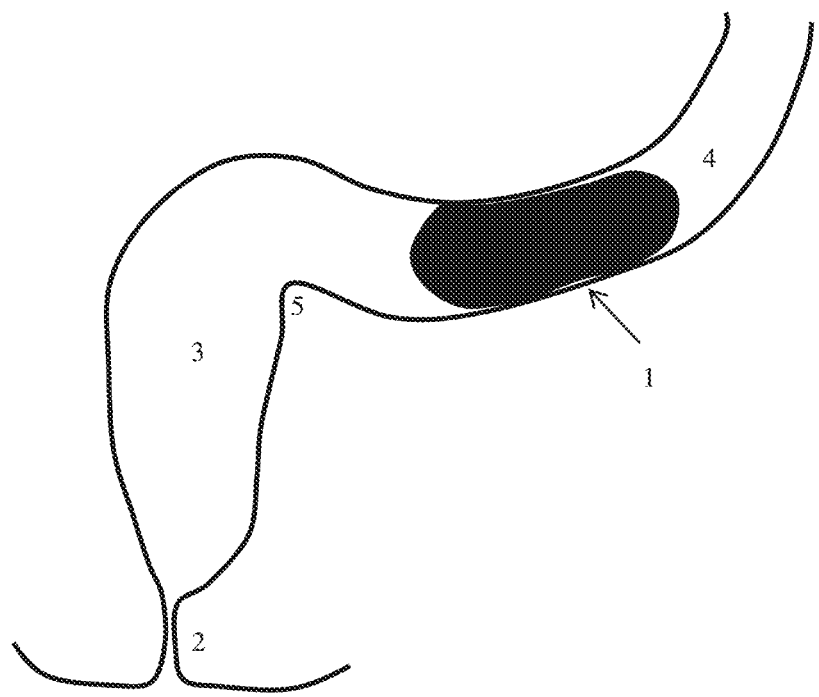
FIGS. 1A, 1B, and 1C: Sketches of the smart artificial pellet (an exemplary device or apparatus of the present disclosure) inside the intestine at different locations.

An overview of the features, functions and/or configurations of the components depicted in the various figures will now be presented. It should be appreciated that not all of the features of the components of the figures are necessarily described. Some of these non-discussed features, such as various couplers, etc., as well as discussed features are inherent from the figures themselves. Other non-discussed features may be inherent in component geometry and/or configuration.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

An object of the present disclosure is to record important physiological and pathophysiological parameters during defecation and to overcome disadvantages of conventional technologies. The various figures show several preferred embodiments of the invention. However, the shown embodiments in the figures are merely examples of embodiments. Other embodiments can be either more advanced or simplifications of the illustrated examples. Various embodiments of the invention include an electromechanical device to be inserted into a part of the gastrointestinal tract, preferable in the sigmoid colon with the purpose of recording parameters before and during defecation (in the remaining part of the document the electromechanical device is called smart artificial pellet or abbreviated SAP). The SAP consists in the preferred embodiment of one, two, or all of the following:

a) A central support that stabilizes and supports the whole device but yet provides the needed bending flexibility for the smart artificial pellet to have comparable mechanical properties to normal feces.

b) The core of the artificial fecal pellet where the core material can be solid or preferably semi-solid in order to make the pellet as physiological as possible. In other words, the SAP may be compressible and bendable as normal feces. Several electronic devices such as pressure sensors, force sensors, deformation sensors, accelerometers, gyroscopes, position sensors, miniature cameras and other devices can be embedded in the surface or in the interior of the core material for recording of relevant data variables such as position, velocity, acceleration, trajectory, pressure distribution, force and deformation. The list of sensors is not complete, basically the device can contain any sensor that is small enough to be embedded in the pellet. The core material or the central support may also contain an energy source like a battery and storage unit or wireless transmitter for data recorded by the sensors. The core material may be expandable and compressible according to which solution is best and the surface may be customized to obtain an optimal geometry and surface. For example, in an embodiment where the outer structure as mentioned below is not implemented, it will be preferable that the surface properties of the core imitate the surface properties of feces with respect to shear stress, viscosity and resistance to flow. Typically the core will be 2-10 cm long and 1-6 cm in diameter after insertion into the intestine but in some embodiments it may have other dimensions, both smaller or larger.

c) An outer sizable structure that in preferred embodiments is a bag embracing the core material and containing liquid or gas. In preferred embodiments the diameter of the structure after expansion is 3-10 cm in diameter but it may be smaller or larger in some embodiments. The purpose of expanding the structure is to create a size that is physiological after insertion and to create an urge to defecate. Needless to say the SAP may be smaller or larger and not necessarily spherical or elliptical, it can take any other preferred shape according to the design of the structure. The bag material may be customized to obtain an optimal geometry and surface. For example it will be preferable that the surface properties imitate the surface properties of feces with respect to shear stress, viscosity and resistance to flow.

In a preferred embodiment the SAP is 3-10 cm long, flexible in bending, and compressible in various directions in order to imitate normal feces. The device is comprised of a wireless intraluminal solid or semisolid bolus recording multiple signals such as pressures, forces, deformation, location, velocity acceleration, and direction. From one and up to several hundred sensors may be imbedded in the SAP to provide a detailed analysis of the defecation process, including geometry, location, and the forces the device is exposed to. The device can contain gyroscopes for data on the orientation, e.g. in both ends of the device to provide data on angling. The SAP may in preferred embodiments also contain sensors for tracking in a scanner or similar device. An exemplary embodiment is electromagnetic sensors that can be tracked to provide a trajectory of the path the bolus follows during the passage in the sigmoid colon and rectum during defecation. The displacement data together with the detailed distribution of surface parameters will provide multiple options for analysis of the system properties, e.g. color contour graphs of the bolus in relation to the displacement of it. The device will in preferred embodiments contain wireless data transmission units, memory for data storage, and energy source like a small battery.

Some sensors in the SAP may be force or deformation sensors based on strain gauge technology. They may also be based on measurement of electrical impedance in an impedance planimetric chamber system for measurement of cross-sectional area or diameter, or a system based on light (wave displacement or frequency). One solution is the use of pressure transducers embedded in the surface. The invention is however not restricted to the above solutions, i.e. they may be based on other technologies. It is noted that the electrodes used to obtain impedance measurements can include electrodes used to excite an electric field and electrodes (positioned within the excitation electrodes, namely the electrodes used to excite the field) used to detect the electric field so to obtain the impedance measurements, whereby said measurements can be used to determine cross-sectional area, diameters, and the like.

The sensors are connected with wires or wireless to one or more data acquisition systems that will amplify and condition the signals. Software (included within various hardware elements of the present disclosure, as appropriate, such as stored on a storage medium and accessed using a processor, on a data storage device, and/or included within various elements shown in FIG. 3) will be used for display and analysis, for example of color contour plots or other plots showing the passage of the device and the SAP geometry, and displacements/deformation. The data can be related to other recorded signals or to the stimulation magnitude imposed by various means.

The uniqueness of the invented SAP is that it has completely different purpose, structure and content than other known technologies for measurement inside the gastrointestinal tract. Technologies such as catheters with pressure sensors as used in high-resolution manometry and radiographic methods such as defecography are obviously very different. Ingestible capsules have been marketed with the purpose of measuring pressure and pH and for photographing the gastrointestinal tract from inside. Such capsules are however rather small and are not expandable and without sensors for measurement of force-deformation relations and these capsules do not provide detailed data on the defecation process.

Figure 1B:
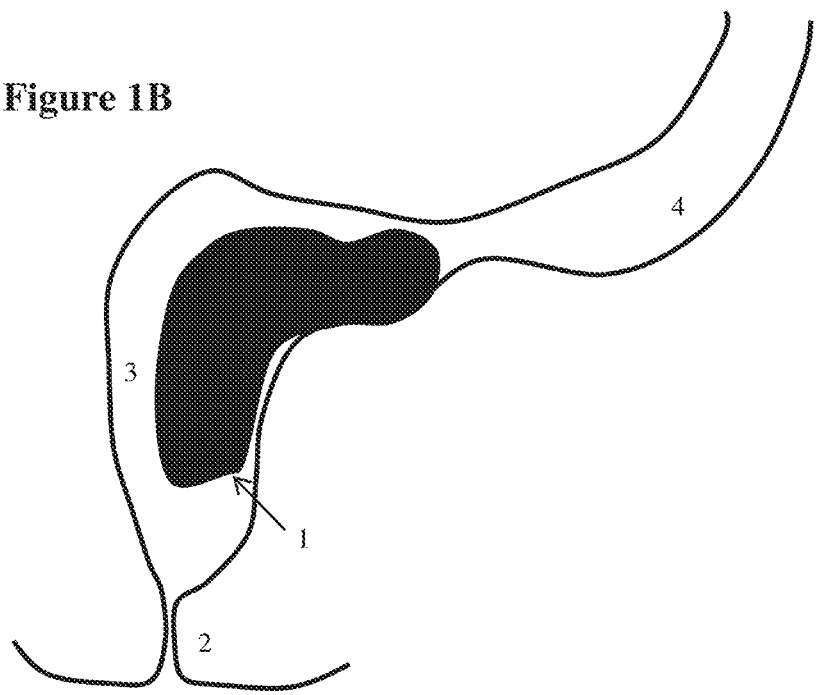
Figure 1C:
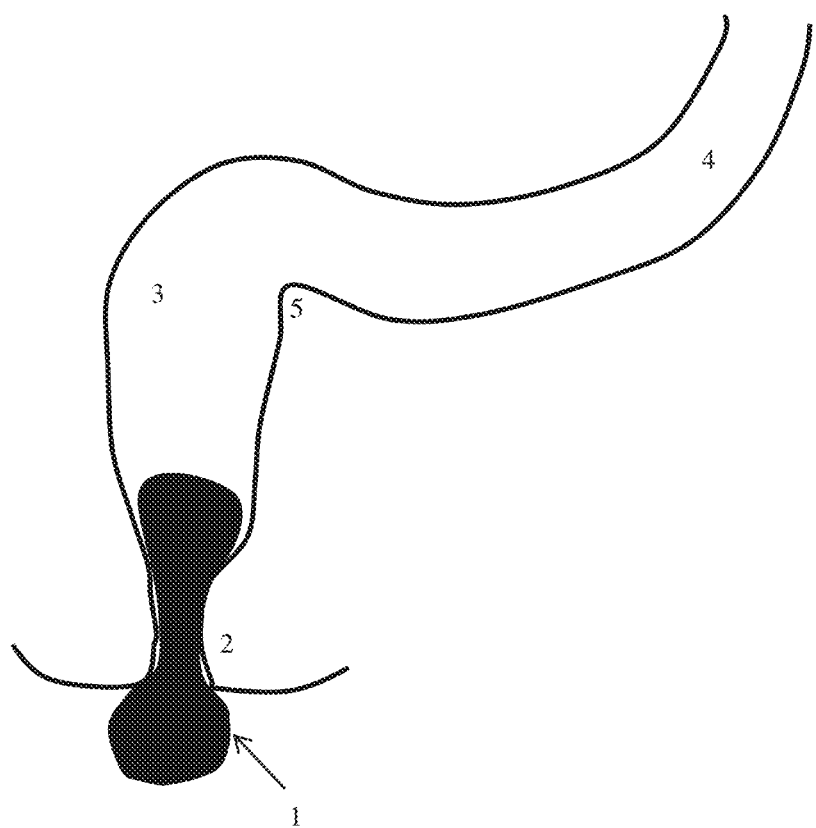
Figure 2A:
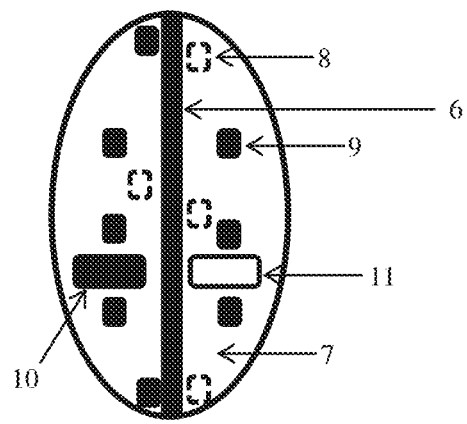
FIGS. 2A, 2B, 2C, 2D, and 2E: Sketches of different embodiments of the smart artificial pellet, in all of them various sensors are shown and other electronic components such as energy supply, memory unit, and transmitter.
Figure 2B:
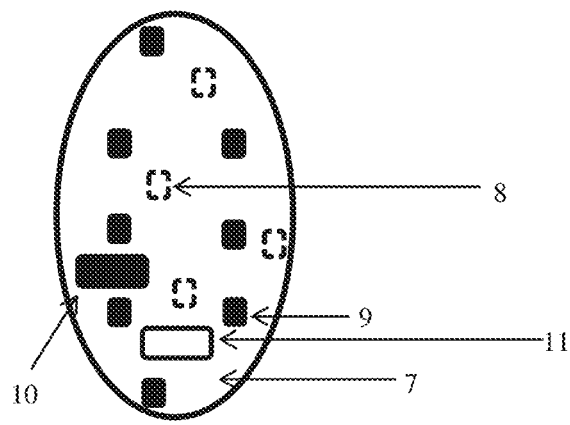
Figure 2C:
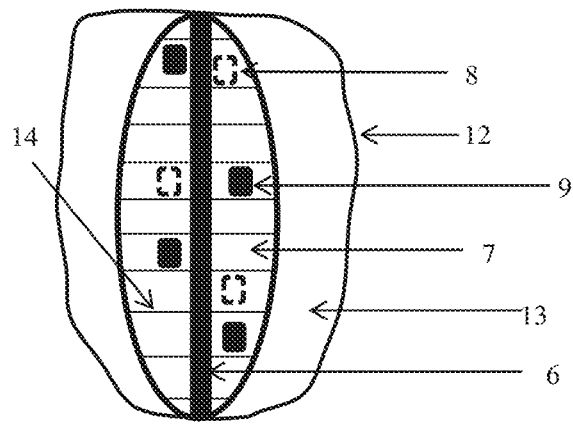
Figure 2D:
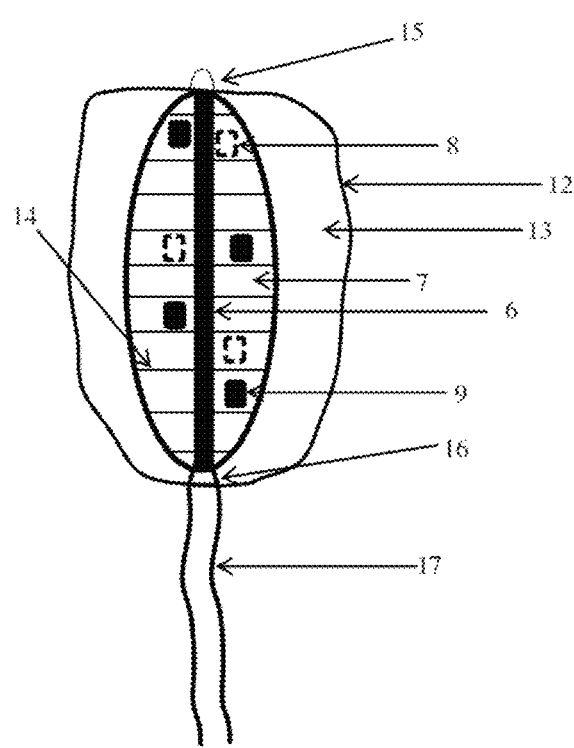
Figure 2E:
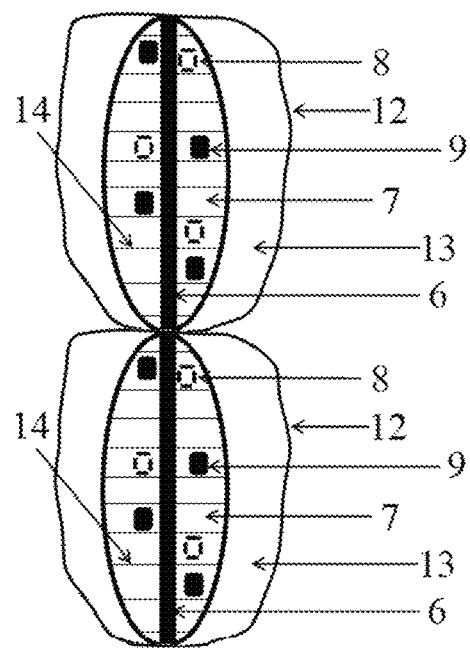
Figure 3:
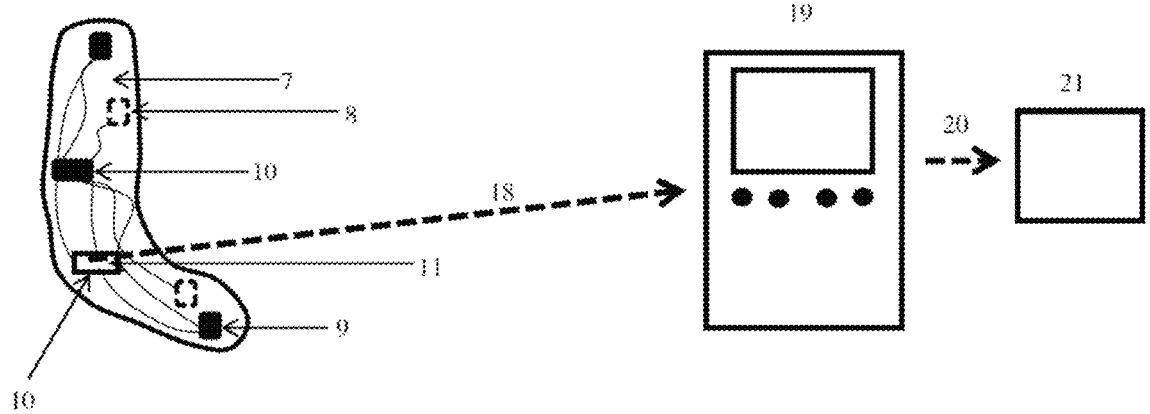
FIG. 3 shows a sketch of a system showing the smart artificial pellet, a receiver unit outside the body and a computer or other unit for storage, analysis and display of data. The elements as shown in this figure include 7: pellet solid or semi-solid material, 8: sensors embedded in the interior of the smart artificial pellet, 9: sensor on the surface of the smart artificial pellet, 10: battery or energy source connected through wires to all sensors, transducers and transmitter, 11: data storage device or wireless transmitter to outside unit, 18: wireless transmission to unit outside the body, 19: receiver unit with or without display; 20: wireless or wired transmission to computer or analysis unit, and 21: computer or analysis/graphics unit.
Figure 4:
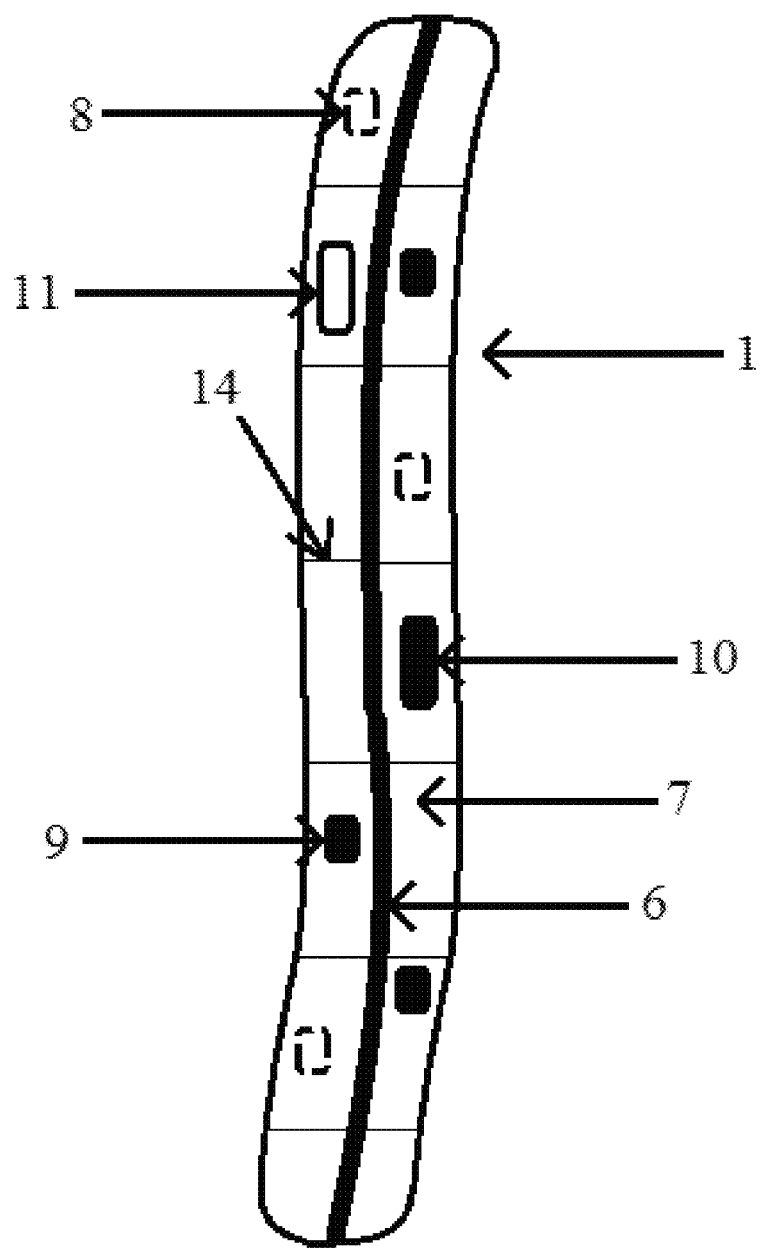
FIG. 4 shows an additional embodiment of the smart artificial pellet, having a relatively long and narrow "worm-like" configuration which can be swallowed by the patient or inserted by endoscope or surgery. The elements as shown in this figure include 1: smart artificial pellet device (SAP), 6: central stabilizing flexible or non-flexible core rod, 7: pellet solid or semi-solid material, 8: sensors embedded in the interior of the artificial fecal pellet, 9: sensor on the surface of the artificial fecal pellet, 10: battery or energy source connected through wires to all sensors, transducers and transmitter, 11: data storage device or wireless transmitter to outside unit, and 14: electrodes for impedance planimetric measurement of cross-sectional areas.
Figure 5A:
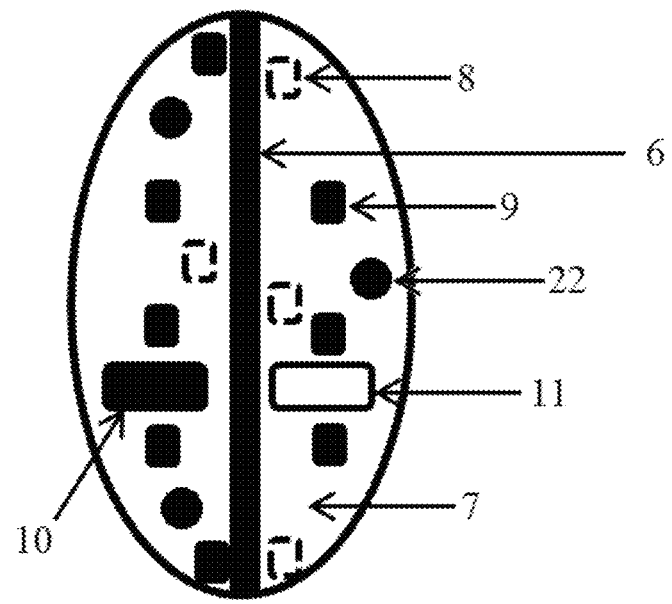
FIGS. 5A and 5B show different embodiments of the smart artificial pellet.
Figure 5B:
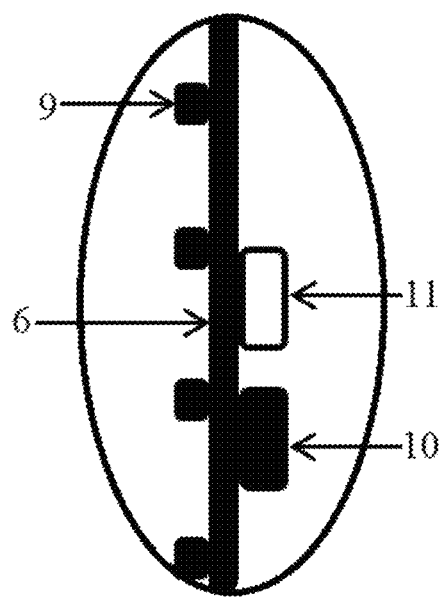
Figure 6A:
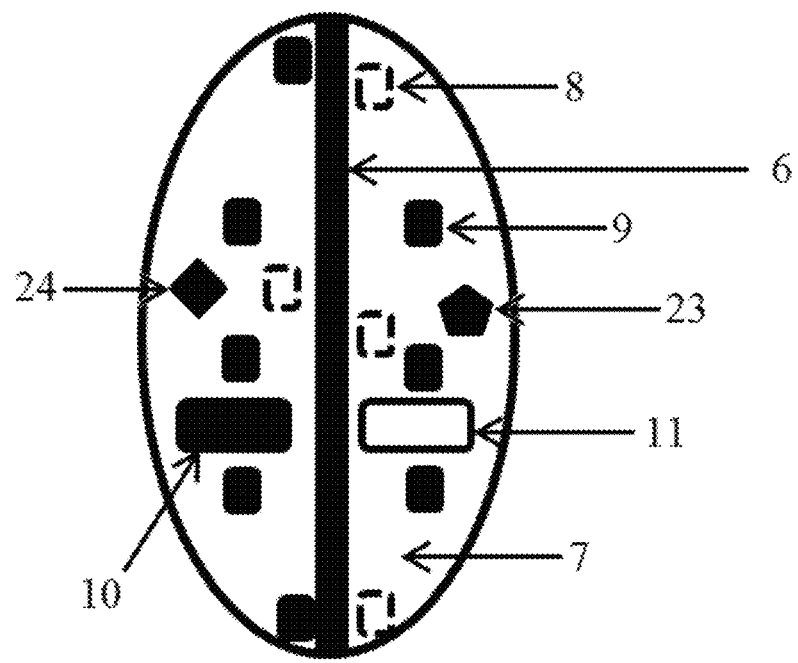
FIGS. 6A and 6B show different embodiments of the smart artificial pellet.
Figure 6B:
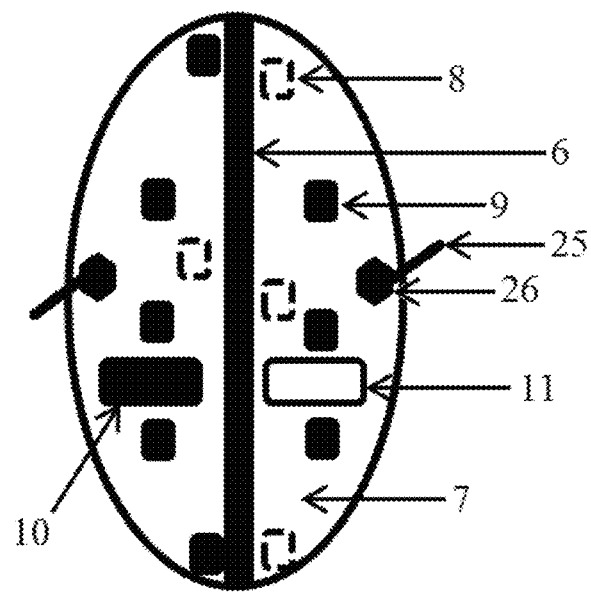
Figure 7A:
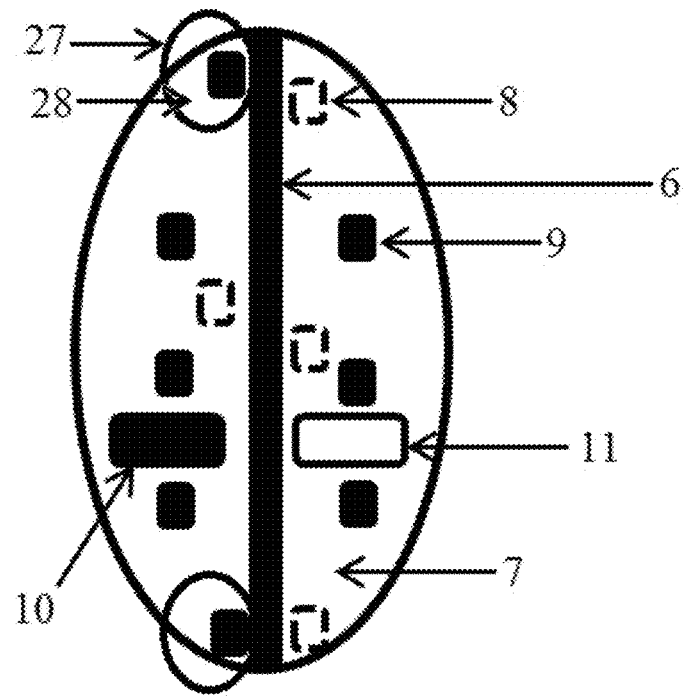
FIGS. 7A and 7B show different embodiments of the smart artificial pellet.
Figure 7B:
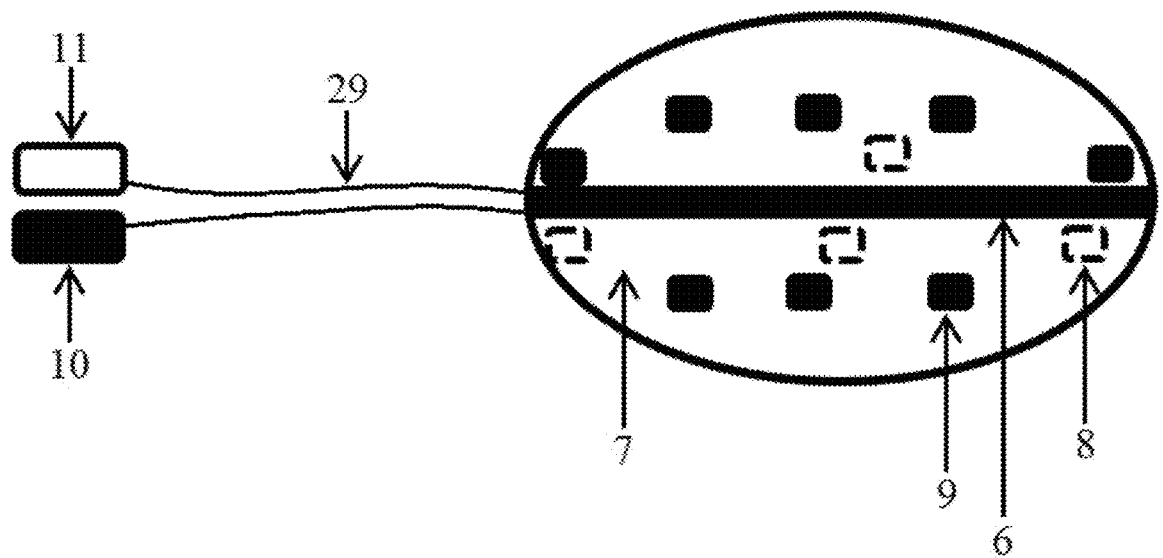

The preferred target organ is the sigmoid colon and rectum but it may apply to any part of the gastrointestinal tract and even to other organs. The device must be sized according to the size of the organ to be placed in. The abovementioned embodiments and figures are merely examples, i.e. the listing is not exclusive and many variants of the device may be produced, manufactured and commercialized. FIGS. 1-3 show several examples of embodiments. Various SAP embodiments can be used multiple times with multiple patients, whereby new sterile balloons or bags, such as shown in FIG. 2C, could be used prior to re-use of the device.

Additional embodiments of a SAP of the present disclosure can have a relatively long and narrow "worm-like" configuration which can be swallowed by the patient or inserted by endoscope or surgery. Such an embodiment can pass the entirety or part of the gastro-intestinal tract. Such an embodiment may be the same or approximately the same length as other embodiments, or it may be longer, whereby the electrodes can obtain impedance data along a greater overall length of the SAP as may be desired.

Various SAP embodiments can also have one or more electrical stimulating sensors on the surface of the artificial fecal pellet. These electrical stimulating sensors can electrically stimulate (deliver an electrical signal to) portions of the gastrointestinal tract, such as the gastrointestinal wall and/or nearby nerves, such as the pudendal nerve close to the rectum, as pudendal nerve stimulation initiates the recto-anal inhibitory reflex. Additional SAP embodiments can operate without a distensible shell like a balloon or bag that can be inflated, whereby the sensors embedded in the interior of the artificial fecal pellet, the battery, and the data storage device or wireless transmitter to outside unit are positioned on or within the central stabilizing flexible or non-flexible core rod. Such embodiments can have a series of pressure sensors on the core to provide for high-resolution manometry during the passage of the device through the gastrointestinal tract.

Various SAP embodiments can further comprise at least one sensor configured as a camera and a light source, such as a flash, so to provide light so that the camera can obtain images within the patient. SAP embodiments can also be configured to make movements, and thereby crawl, through portions of the gastrointestinal tract, such as the colon, by itself. Furthermore, various embodiments can be used to obtain tension and/or strain data, by way of operation of sensors inside and/or on the surface of the SAP, which can be computed and viewed in real-time or offline. SAP embodiments can also be used to give a measure of the shear force or shear stress during movement of the SAP through the gastrointestinal tract.

SAP embodiments can also comprise a bag or balloon positioned around the front and rear (proximal and distal) sensors configured as pressure transducers in order to measure a more reliable pressure during expulsion. In various embodiments, certain components referenced herein can be external to the pellet but connected to the pellet using thin wires. Such components can be placed outside the anal canal and connected using the wires passing the anal canal to the device. Various components, such as the battery and/or wireless transmitter, can be on the outside and connected to the SAP using wires to save overall space within the device itself.

In various embodiments, the pellet further comprises an application-specific integrated circuit (ASIC) whereby one or more of the embedded sensor, the battery or energy source, the data storage device or wireless transmitter, and/or the electrodes for impedance measurements, are positioned thereon and/or otherwise coupled thereto. Various SAP embodiments can also have one or more magnets or magnetically-attractive elements can be used so to magnetically attach to an endoscope during insertion and/or to the tube for filling the outer structure such as a balloon.

Example of use of the invention. The physician in a specialized unit for defecatory disorders unpacks the device, make sure the battery is charged and that the SAP is functioning with recordings to an external device. The patient has beforehand been asked to empty the rectum for feces. The physician makes an endoscopy in the rectum and sigmoid and during that procedure the SAP is inserted and pushed or pulled up to the preferred location. The SAP can be expanded either by pulling it out from an embracing structure or by filling the bag until the patient feels urge to defecate. The physician disconnects the tube to the SAP and pulls it out. This leaves the SAP in the sigmoid colon without any connecting wires. The endoscope is slowly pulled out and the patient is allowed to defecate. Measurements are made by the device before and during defecation and the data may be visualized in real time by the receiver unit outside the person being studied. Detailed analysis may take place offline. Simultaneously the patient may record symptoms such as pain during the process. In case the patient cannot defecate the SAP, then it may be necessary to remove it in due time by endoscopy in a clinic or hospital. The physician or a technician will analyze the data and based on the analysis proper diagnosis and plan for treatment will be made. This is one exemplary use of a device of the present disclosure, noting that other uses (depending on device configuration and componentry) would be used as referenced herein.

The measurements referenced above (such as various mechanics and displacement) may also be dependent upon the diameter of the smart artificial pellet device (SAP) and/or the diameter or size of the inflatable balloon or bag. Each patient has a unique tension-length relation that can be determined by varying the diameter of the SAP and/or the balloon or bag and recording the corresponding tension (such as by way of pressure sensors). The tension-length relation can be calibrated for each patient to determine the appropriate diameter of the SAP and/or the balloon or bag used for that patient.

For example, the balloon or bag can be inflated at different pressures and/or volumes, and the diameter of the balloon or bag can be recorded as a circumference ($\pi \times$ diameter) along with the tension (pressure$\times$diameter/2) to produce a tension-length relation. The resultant curve should be parabolic in shape, with the diameter corresponding to the ascending point of the curve selected for each patient. These objective measurements can complement the subjective measurements referenced below.

Various cross-sectional areas or diameters, as referenced herein, can be determined by impedance planimetry. In many cases, the balloon or bag can be filled until the patient feels the urge or need to defecate (a subjective measurement), and then the tube used to fill the bag can be disconnected and the patient can then try to defecate the SAP. Tension and diameter measurements can be obtained during filling and during the defecation process, and the tension-length properties at various sensation levels, such as the urge to defecate that the pain threshold, can be obtained as well.

As referenced herein, pressure sensors or transducers can be positioned or placed on a surface of the device (also referred to herein as SAP), such as being positioned upon or embedded within a surface of a bag or a balloon of said device. Such a pressure sensor or transducer would be a "9: sensor on the surface of the artificial fecal pellet," and such a balloon or bag would be a "12: distensible shell like a balloon or bag that can be inflate," as referenced herein and shown within the figures. Should multiple pressure sensors or transducers be used, said pressure sensors or transducers could each be positioned upon or embedded within a surface of the bag or balloon, and be configured to obtain multiple pressure measurements on the surface of the bag or balloon at the locations of said sensors.

Figure 8A:
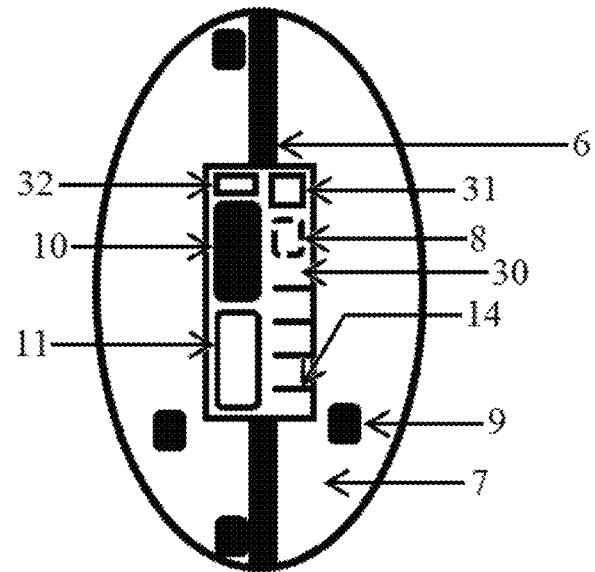
FIGS. 8A and 8B show different embodiments of the smart artificial pellet.
Figure 8B:
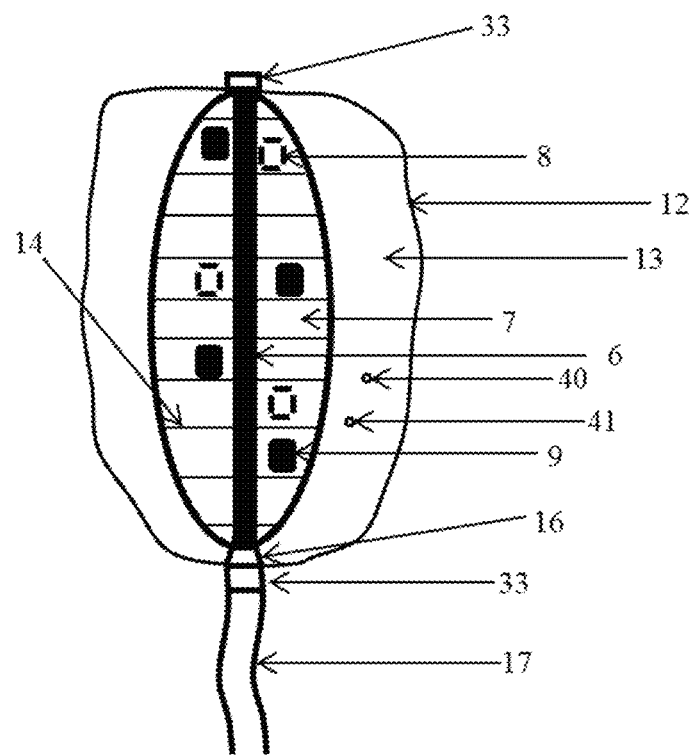

Furthermore, and in various device embodiments referenced herein, the balloon or bag (12: distensible shell like a balloon or bag that can be inflated) having a liquid or gas therein (13: liquid or gas inside the shell) can be inflated, such as by way of self-expansion therein, due to a gas generated by a chemical reaction within said balloon or bag. For example, and in various embodiments, a first chemical within the balloon or bag could react with a second chemical within the balloon or bag (whereby said chemicals could be gasses, liquids, or solids), whereby a reaction of the first chemical and the second chemical releases a gas that causes the balloon or bag to expand. Amounts of the first chemical and the second chemical could be tightly controlled so that the amount of gas produced from the reaction is controlled as desired. The first chemical and the second chemical are shown in FIG. 8B, but it is understood that said chemicals, such as gases or liquids or small solids, may not be readily visible within the balloon or bag.

Other device embodiments of the present disclosure could be sized and shaped so to be swallowed. Various measurements, such as impedance, pressure, and the like, as referenced herein, could be obtained in the mouth, the esophagus, the stomach, the intestines, at the anus, and various junctions/sphincters along said pathway. In such embodiments, the devices (SAPs) would be sized and shaped to be swallowed by the patient, such as being referred to as miniaturized devices.

In various device embodiments, application-specific integrated circuit or printed circuit 30 may be configured to measure electrical/electromyography (EMG) activity (exemplary data) within the colon, for example. Said data can, in various embodiments, be obtained in addition to various mechanical measurements, such as pressure data, impedance data, cross-sectional area (CSA) data, etc., obtains as referenced herein, in addition to, for example potential gyroscope-based angles obtained using one or more sensors embedded in the interior of the artificial fecal pellet 8 or sensors on the surface of the artificial fecal pellet 9, configured as gyroscopic sensors or gyroscopes.

In at least one embodiment of a device of the present disclosure, said device is configured to deliver electrical current to stimulate motility of the colon, such as to, for example, induce defecation for individuals with constipation, and the like. In such an embodiment, sensors embedded in the interior of the artificial fecal pellet 8, sensors on the surface of the artificial fecal pellet 9, and/or electrodes for impedance planimetric measurement of cross-sectional areas 14 can be configured as electrical stimulating elements so to deliver an electric current, powered by battery or energy source 10, to stimulate motililty of the colon.

As referenced herein, FIGS. 9, 10, 11, 12, 13, and 14 show charts showing the pressure and dimensional changes during expulsion of the device at different stages and data related thereto.

Figure 9:
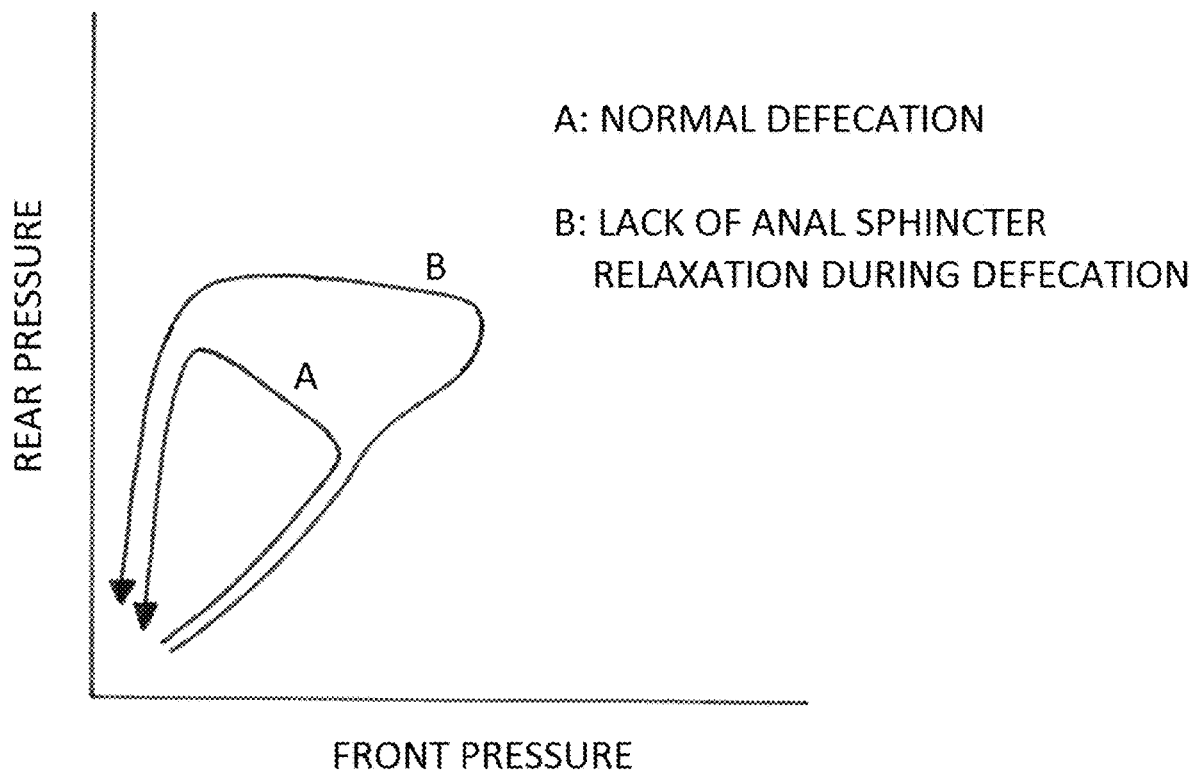
FIGS. 9, 10, 11, 12, 13, and 14 show charts showing the pressure and dimensional changes during expulsion of the device at different stages and data related thereto.
Figure 10:
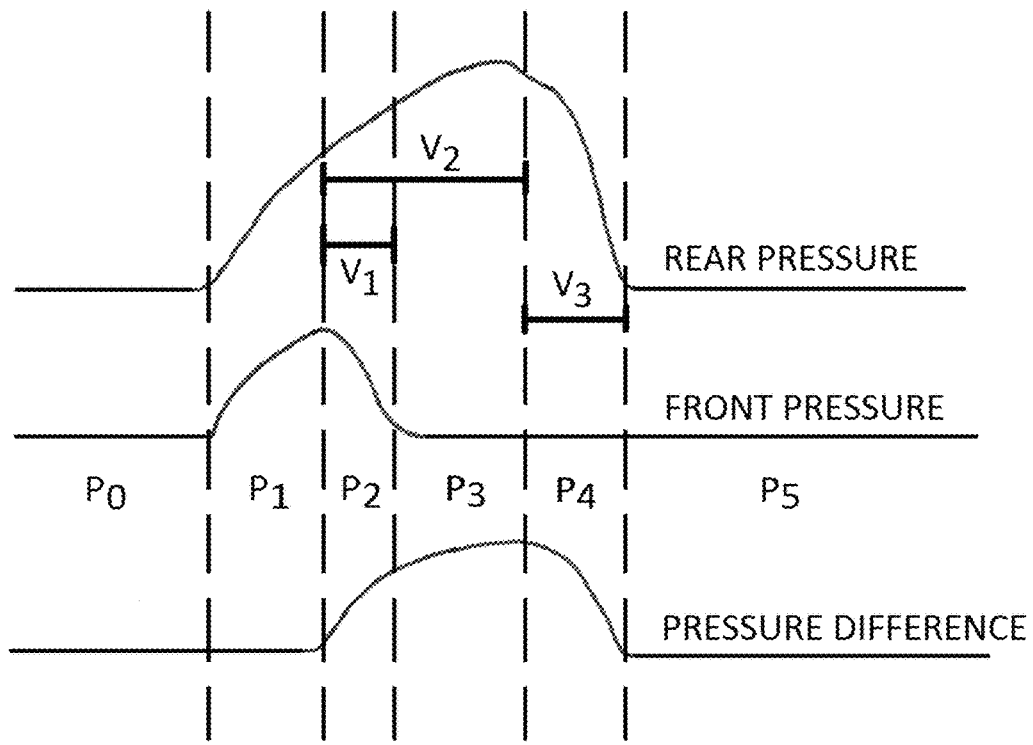
Figure 11:
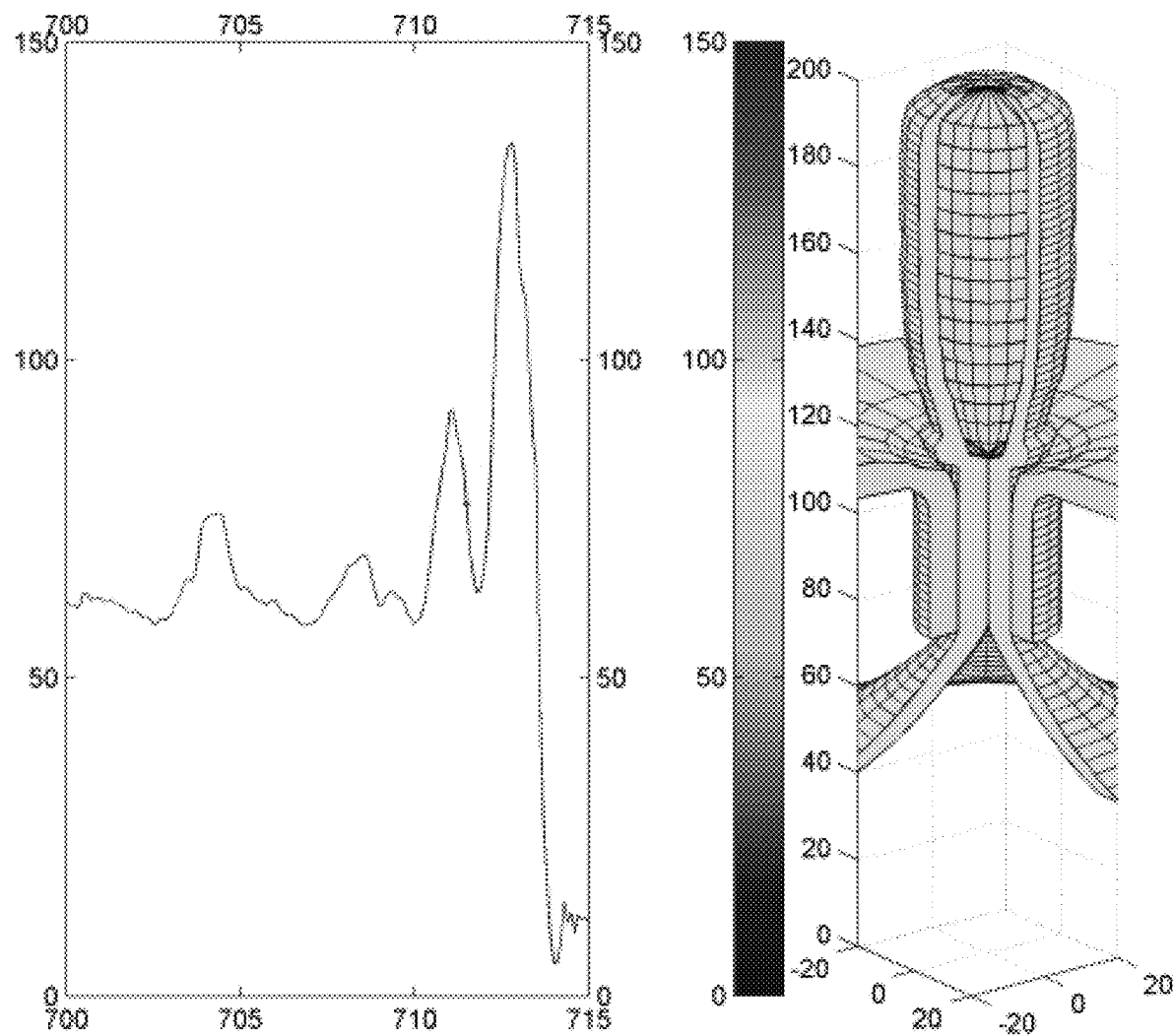
Figure 12:
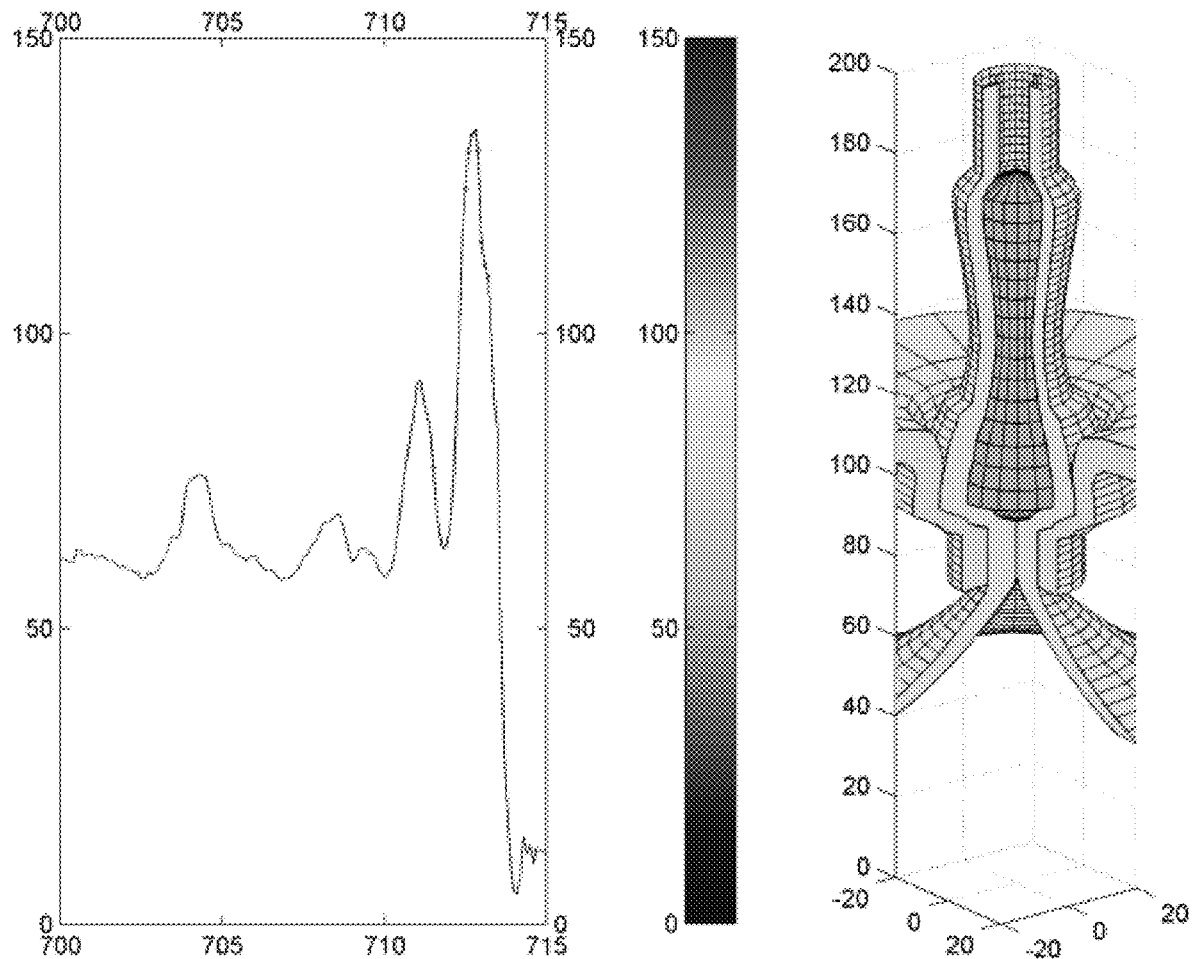
Figure 13:
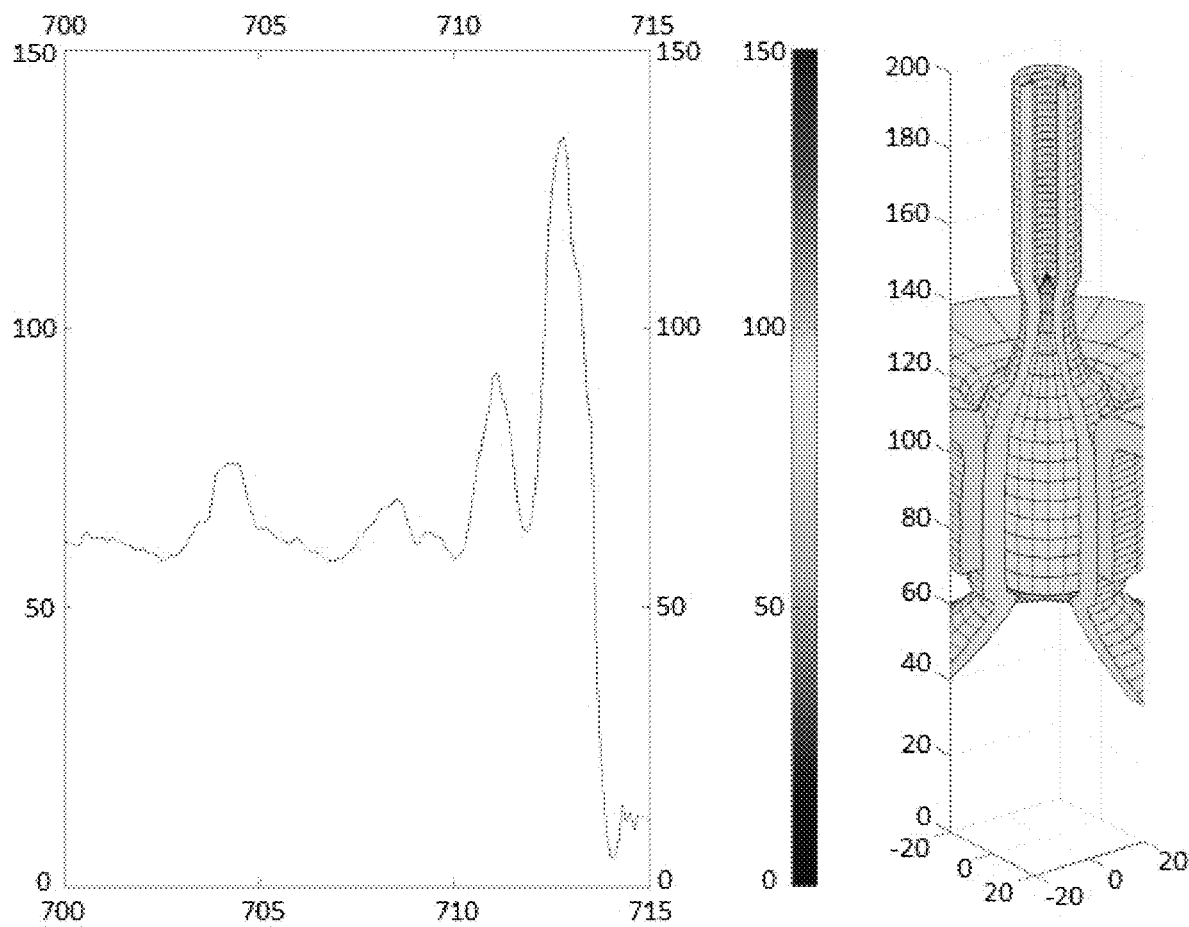
Figure 14:
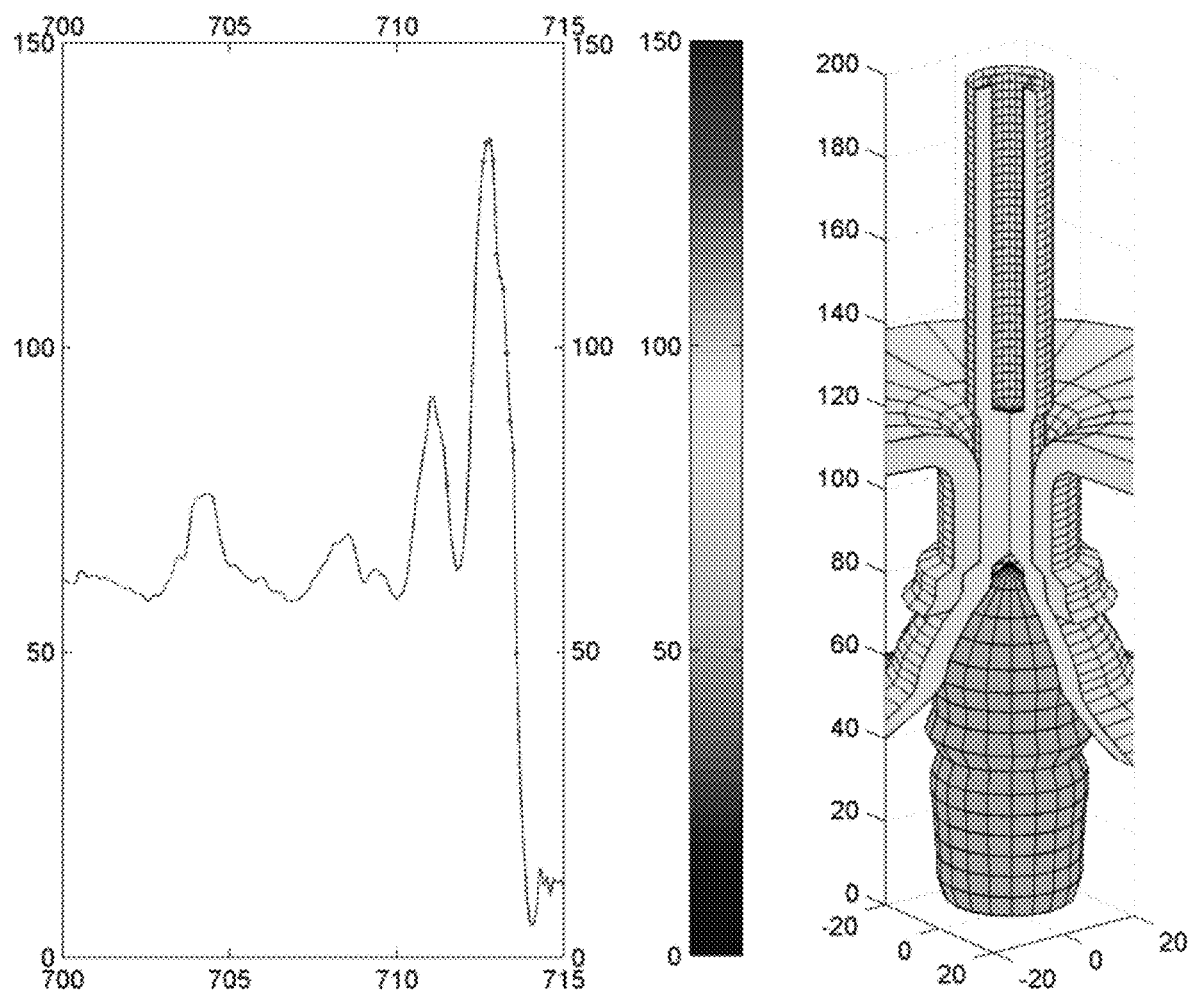

FIG. 9 shows changes in front pressure and rear pressure under normal defecation conditions (line "A") and under a lack of anal sphincter relaxation during defecation (line "B"). As shown therein, the extent of front pressure and rear pressures are relatively higher under a lack of anal sphincter relaxation during defecation as compared to under normal defecation conditions. FIG. 10 shows changes in rear pressure and front pressure (with a net pressure difference shown as well), under a pre-expulsion (pre-defecation) phase, an increase in abdominal pressure, anal sphincter relaxation, the front out of the anal canal, rear end passage, and post-expulsion. As shown therein, front pressure increases occur earlier in the process than rear pressure increases, and rear pressure increases are relatively higher than front pressure increases. FIGS. 11, 12, 13, and 14 show representations of data before and after excretion of the device, in order during the process, whereby the right side of each figure shows relative downward movement of the device until it is fully expelled, as shown in FIG. 14. Device pressure (pressure detected by the device, or pressure applied to the device by the body during the excretory process) within FIG. 11 is between 50 and 100 but below 100, while device pressure is higher in FIG. 11 (approximately at or above 100), somewhat lower in FIG. 12 (approximately at or below 100), and the lowest in FIG. 13 (approximately at or above 50 but below 100). The left side of each of FIGS. 11, 12, 13, and 14 show X-Y plots (front pressure vs rear pressure) which will create loop curves where the magnitude of the pressures and the shape of the loop will show normal patterns of defecation as well as specific patterns for defecation in patients with obstructed defecation or with fecal incontinence.

The various embodiments of the present disclosure will provide a wealth of data related to the function of the organ, in particular to the fecal expulsion process. Pressures, dimensional changes and other measures may be displayed as still pictures or as a function of time, such as in video representations or contour plots, such as color contour plots. The data may be analysed further and displayed in multiple ways, as an example the pressures measured at the front end and the rear end of the core may be displayed as X-Y plots (front pressure vs rear pressure) which will create loop curves where the magnitude of the pressures and the shape of the loop will show normal patterns of defecation as well as specific patterns for defecation in patients with obstructed defecation or with fecal incontinence. Another example of analysing the front and rear pressures are to display these pressures as function of time and include calculations of differential pressures. This facilitates dividing the defecation process into multiple phases that indicates various physiological phenomena such as abdominal and rectal muscle contractions, anal sphincter relaxation or paradoxical contraction, velocity of expulsion in the different phases. The abovementioned data can be analysed merely from two pressures since the distance between the pressure sensors are known. It is clear that the arsenal of analysis will increase tremendously when combined with more pressure measurements, dimensional data, gyroscope data and other measures. A very detailed characteristic of gastrointestinal function, in particular defecation, can be provided.

While various embodiments of devices and methods for using the same have been described in considerable detail herein, the embodiments are merely offered as non-limiting examples of the disclosure described herein. It will therefore be understood that various changes and modifications may be made, and equivalents may be substituted for elements thereof, without departing from the scope of the present disclosure. The present disclosure is not intended to be exhaustive or limiting with respect to the content thereof.

Further, in describing representative embodiments, the present disclosure may have presented a method and/or a process as a particular sequence of steps. However, to the extent that the method or process does not rely on the particular order of steps set forth therein, the method or process should not be limited to the particular sequence of steps described, as other sequences of steps may be possible. Therefore, the particular order of the steps disclosed herein should not be construed as limitations of the present disclosure. In addition, disclosure directed to a method and/or process should not be limited to the performance of their steps in the order written. Such sequences may be varied and still remain within the scope of the present disclosure.

The invention claimed is:

1. A device, consisting essentially of:
    a single flexible central support;
    a first bag or balloon surrounding at least part of the flexible central support; and
    a first plurality of sensors positioned upon or embedded within a surface of the first bag or balloon, each of the first plurality of sensors positioned a known distance from each other;
    wherein the first plurality of sensors are configured to obtain pressure measurements on the surface of the first bag or balloon when the device is operated within a mammalian gastrointestinal tract; and
    wherein the flexible support extends from at least a first end to a second end of the bag or balloon.

2. The device of claim 1, wherein the first bag or balloon is configured for self-expansion.

3. The device of claim 1, further comprising a quantity of a first chemical and a quantity of a second chemical within the first bag or balloon.

4. The device of claim 3, wherein a reaction between the quantity of the first chemical and the quantity of the second chemical causes a quantity of a gas to be generated, whereby the quantity of the gas causes the first bag or balloon to inflate.

5. The device of claim 1, further comprising:
    a second bag or balloon surrounding at least another part of the flexible central support; and
    a second plurality of sensors positioned upon or embedded within a surface of the second bag or balloon, each of the second plurality of sensors positioned a known distance from each other;
    wherein the second plurality of sensors are configured to obtain additional pressure measurements on the surface of the second bag or balloon when the device is operated within a mammalian gastrointestinal tract.

6. The device of claim 5, wherein the second bag or balloon is configured for self-expansion.

7. The device of claim 5, further comprising an additional quantity of the first chemical and an additional quantity of the second chemical within the second bag or balloon.

8. The device of claim 7, wherein a reaction between the additional quantity of the first chemical and the additional quantity of the second chemical causes an additional quantity of the gas to be generated, whereby the additional quantity of the gas causes the second bag or balloon to inflate.

9. The device of claim 1, sized and shaped to be swallowed by a mammal.

10. The device of claim 1, further comprising:
a solid or semi-solid material positioned within the first bag or balloon that at least partially surrounds at least part of the flexible central support.

11. The device of claim 1, further comprising:
a first plurality of electrodes configured to obtain impedance measurements indicative of cross-sectional areas at various locations within the first bag or balloon when the device is operated within the mammalian gastrointestinal tract.

12. The device of claim 11, further comprising:
a second plurality of electrodes configured to obtain additional impedance measurements indicative of additional cross-sectional areas at various locations within the second bag or balloon when the device is operated within the mammalian gastrointestinal tract.

13. The device of claim 11, configured to transmit the pressure measurements and the impedance measurements indicative of the cross-sectional areas to an external device configured to receive the pressure measurements and the impedance measurements indicative of the cross-sectional areas and further configured to generate a two-dimensional or a three-dimensional image depicting the pressure measurements and the cross-sectional areas at various locations within the device when the device is operated within the mammalian gastrointestinal tract.

14. The device of claim 11, wherein a first pressure measurement within the pressure measurements is indicative of pressure exerted upon the device by the mammalian gastrointestinal tract prior to excretion, and wherein a second pressure measurement within the pressure measurements is indicative of pressure exerted upon the device by the mammalian gastrointestinal tract during excretion, and wherein the first pressure measurement is higher than the second pressure measurement.

15. A method of obtaining pressure measurements, the method comprising the step of:
positioning the device of claim 1 within the mammalian gastrointestinal tract; and
operating the device to obtain the pressure measurements within the mammalian gastrointestinal tract.

16. A device, consisting essentially of:
a single flexible central support;
a first bag or balloon surrounding at least part of the flexible central support;
a first plurality of sensors positioned upon or embedded within a surface of the first bag or balloon, each of the first plurality of sensors positioned a known distance from each other; and
a quantity of a first chemical and a quantity of a second chemical within the first bag or balloon;
wherein the first plurality of sensors are configured to obtain pressure measurements on the surface of the first bag or balloon when the device is operated within a mammalian gastrointestinal tract;
wherein a reaction between the quantity of the first chemical and the quantity of the second chemical causes a quantity of a gas to be generated, whereby the quantity of the gas causes the first bag or balloon to inflate;
wherein the device is sized and shaped to be swallowed by a mammal; and
wherein the flexible support extends from at least a first end to a second end of the bag or balloon.

17. The device of claim 16, further comprising:
a solid or semi-solid material positioned within the first bag or balloon that at least partially surrounds at least part of the flexible central support.

18. The device of claim 16, further comprising:
a first plurality of electrodes configured to obtain impedance measurements indicative of cross-sectional areas at various locations within the first bag or balloon when the device is operated within the mammalian gastrointestinal tract.

* * * * *